United States Patent [19]

Kausek

[11] Patent Number: 4,991,571
[45] Date of Patent: * Feb. 12, 1991

[54] MODULAR KNEE BRACE FOR CONTROL OF LIGAMENT INSTABILITY

[76] Inventor: James H. Kausek, 31 Stanwood Rd., Swampscott, Mass. 01907

[*] Notice: The portion of the term of this patent subsequent to Oct. 30, 2007 has been disclaimed.

[21] Appl. No.: 343,861

[22] Filed: Apr. 26, 1989

Related U.S. Application Data

[63] Continuation-in-part of Ser. No. 241,588, Sep. 8, 1988.

[51] Int. Cl.⁵ ............................................. A61F 5/00
[52] U.S. Cl. .................................... 128/80 C; 128/165
[58] Field of Search .................... 128/165, 80 C, 80 F, 128/88

[56] References Cited

U.S. PATENT DOCUMENTS

| | | | |
|---|---|---|---|
| 3,387,305 | 6/1968 | Shaffer | 128/80 C |
| 3,581,741 | 6/1971 | Rosman | 128/80 |
| 4,144,592 | 3/1979 | Larson | 128/80 C |
| 4,372,298 | 2/1983 | Lerman | 128/80 C |
| 4,506,661 | 3/1985 | Foster | 128/80 C |
| 4,554,913 | 11/1985 | Womaek | 128/80 C |
| 4,556,053 | 12/1985 | Irons | 128/80 C |
| 4,624,247 | 11/1986 | Ford | 128/80 C |
| 4,632,098 | 12/1986 | Grundei et al. | 128/80 C |
| 4,633,867 | 1/1987 | Kawsek et al. | 128/80 C |
| 4,635,623 | 1/1987 | Chewruest | 128/80 C |
| 4,681,097 | 7/1987 | Pansiera | 128/77 |
| 4,732,143 | 3/1988 | Kausek et al. | 128/80 C |
| 4,733,656 | 3/1988 | Marguette | 128/80 C |
| 4,781,179 | 11/1988 | Colbert | 128/80 C |
| 4,791,916 | 12/1988 | Pacz | 128/80 C |
| 4,802,466 | 2/1989 | Meyers et al. | 128/80 C |
| 4,803,975 | 2/1989 | Meyers | 128/88 |
| 4,805,606 | 2/1989 | McDavid | 128/80 C |
| 4,854,308 | 8/1989 | Drillio | 128/80 C |

Primary Examiner—Edgar S. Burr
Assistant Examiner—Huong Q. Pham
Attorney, Agent, or Firm—Wolf, Greenfield & Sacks

[57] ABSTRACT

A knee brace for control of ligament instability in all planes having thigh and shin cuffs, a polycentric hinge on the lateral side of the knee, and a pivoting articulation plate on the medial side of the knee. The cuffs are attached to the leg by non-stretchable straps and provide anterior-posterior stability. The medial pivot plate stabilizes the brace on the medial side of the knee and in combination with the lateral hinge and a lateral plate provides medial-lateral stability. In another embodiment the cuff is replaced by thigh plates with adjustable connecting means to accommodate different sized thighs. The thigh plates, medial plate and shin cuff are shaped to permit interchangeable use on left and right knee braces. Adjustable front and rear straps connect the medial pivot plate and shin cuff for providing ligament stability and adjustability as to various knee widths.

8 Claims, 16 Drawing Sheets

MODULAR KNEE BRACE FOR CONTROL OF LIGAMENT INSTABILITY

This is a continuation in part application of co-pending and commonly assigned Ser. No. 07/241,588, filed Sept. 8, 1988, entitled Knee Brace For Control Of Ligament Instability, by James H. Kausek.

BACKGROUND OF THE INVENTION

This invention concerns a knee brace for controlling ligament instability, and more particularly to a knee brace having thigh and shin cuffs joined by a polycentric hinge on the lateral side of the brace and a pivotal articulation plate at the medial side of the knee.

In a further embodiment, the invention concerns a knee brace including a plurality of separate thigh plates adjustably connected together, a medial articulation plate, and a shin cuff, all of which components are modular and can be used on either a left or right knee brace.

When the ligaments surrounding the knee have been traumatized by injury or by surgery, a supporting brace is used to provide stability while still allowing movement of the knee. The brace should provide stability when forces are applied to the knee in the medial and lateral (side) planes and in the anterior (front) and posterior (rear) planes. In addition, the brace should provide rotational stability so as to prevent excessive axial rotation of the tibia with respect to the femur. The brace should also prevent forward movement of the tibia with respect to the femur, a function provided in the normal knee by the anterior cruciate ligament.

A knee brace for control of ligament instability is described in U.S. Pat. No. 4,633,867 to Kausek et al. That brace includes a thigh cuff, a shin plate, and a rear calf cuff. In that brace two polycentric hinges are provided at the medial and lateral sides of the brace. While use of polycentric hinges on both sides of the knee provides good ligament control, the movement of the knee is somewhat restricted.

Knee braces having a lateral hinge, but no medial hinge, are often worn by football players to prevent injury. They may also be used for rehabilitation or to support a knee which exhibits chronic instability. The lateral hinge, which may be monocentric or polycentric, has upper and lower lateral plates which are either taped to the leg or inserted in a wrap-around neoprene sleeve by VELCRO attachment straps with closures. This brace provides greater support when taped to the leg, but taping is uncomfortable and not practical for daily use. The brace provides less support when attached via the neoprene sleeve.

It would thus be desirable to provide a knee brace which provides good ligament control while allowing a natural range of movement of the knee, and which is comfortable to wear and easily removable for daily use. It would also be desirable to provide a brace which offers some adjustability as to size and thus can be sold as an of-the-shelf item. It would also be cost-desirable to provide a brace with modular components which can be used on both left and right knee braces. These and other features are provided by the knee brace of the present invention.

SUMMARY OF THE INVENTION

The first and second embodiments of the knee brace of this invention include upper and lower cuffs positioned above and below the knee which are attached to the leg by substantially non-stretchable cuff straps. A lateral hinge having upper and lower hinge arms and at least one pivot point is positioned at the lateral side of the knee, with the upper hinge arm connected to a lateral portion of the upper cuff and the lower hinge arm connected to a lateral portion of the lower cuff. A medial articulation plate is positioned at the medial side of the knee which has an inner surface for engaging the medial knee joint. The medial plate is pivotally connected to the upper cuff and connected by straps to the lower cuff. The upper and lower cuffs and the non-stretchable cuff straps provide anterior-posterior stability to the knee joint while the lateral hinge and medial plate provide medial-lateral stability.

The upper and lower cuffs each comprise a hard outer shell for rigidity and strength with a softer, non-abrasive lining for comfort. Each cuff is shaped to engage three sides of the leg and is releasably attached thereto by non-stretchable straps with adjustable fasteners. The hard molded shell provides a rigid framework in the vertical direction for secure attachment and positioning of the upper and lower arms of the polycentric hinge on the lateral side of the brace. Preferably, a lateral plate is provided for engaging the lateral side of the knee, which plate may be attached either to the hinge or to a cover on the hinge.

In order to provide some adjustability as to size, the hard and substantially rigid molded shells of the upper and lower cuffs have some medial-lateral flexibility to accomodate legs of varying girth. The soft foam liner of the cuffs also accomodates differences in leg girth. A series of vertically aligned apertures are provided on the lateral portions of the upper and lower cuffs for selected attachment of the hinge arms to further provide adjustability as to size.

In a third embodiment of the knee brace of this invention, instead of an upper thigh cuff there are provided four separate thigh plates positionable on the anterior, posterior, medial and lateral parts of the thigh. Each of these plates is symmetrical and along with a symmetrical shin cuff allow interchangeable use on a left or right knee brace to thereby substantially reduce the manufacturing cost.

The anterior thigh plate is connected to the medial and lateral thigh plates by adjustable straps. The posterior thigh plate is adjustably connected at opposing ends to the medial and lateral thigh plates by three alternative pairs of apertures disposed in anterior to posterior relation. The posterior thigh plate is arcuate so that selective use of the anterior, central, or posterior sets of apertures provides adjustability both as to width and depth in accomodating different sized thighs.

Furthermore, in the third embodiment the medial articulation plate is connected at an upper pivot point to the medial thigh plate and at a lower connecting point, via two adjustable straps, to the shin cuff. A front strap extends from the medial plate through a loop on an anterior portion of the shin cuff and terminates at a lateral portion of the shin cuff. A rear strap extends from the medial plate around the back of the knee to a lateral portion of the shin cuff. These straps connect the thigh plate and shin cuff at the medial side of the knee for improved anterior-posterior stability and medial-lateral stability and provide adjustability to accomodate different knee widths and angles.

DETAILED DESCRIPTION OF THE PREFERRED EMBODIMENTS

Figure 1:
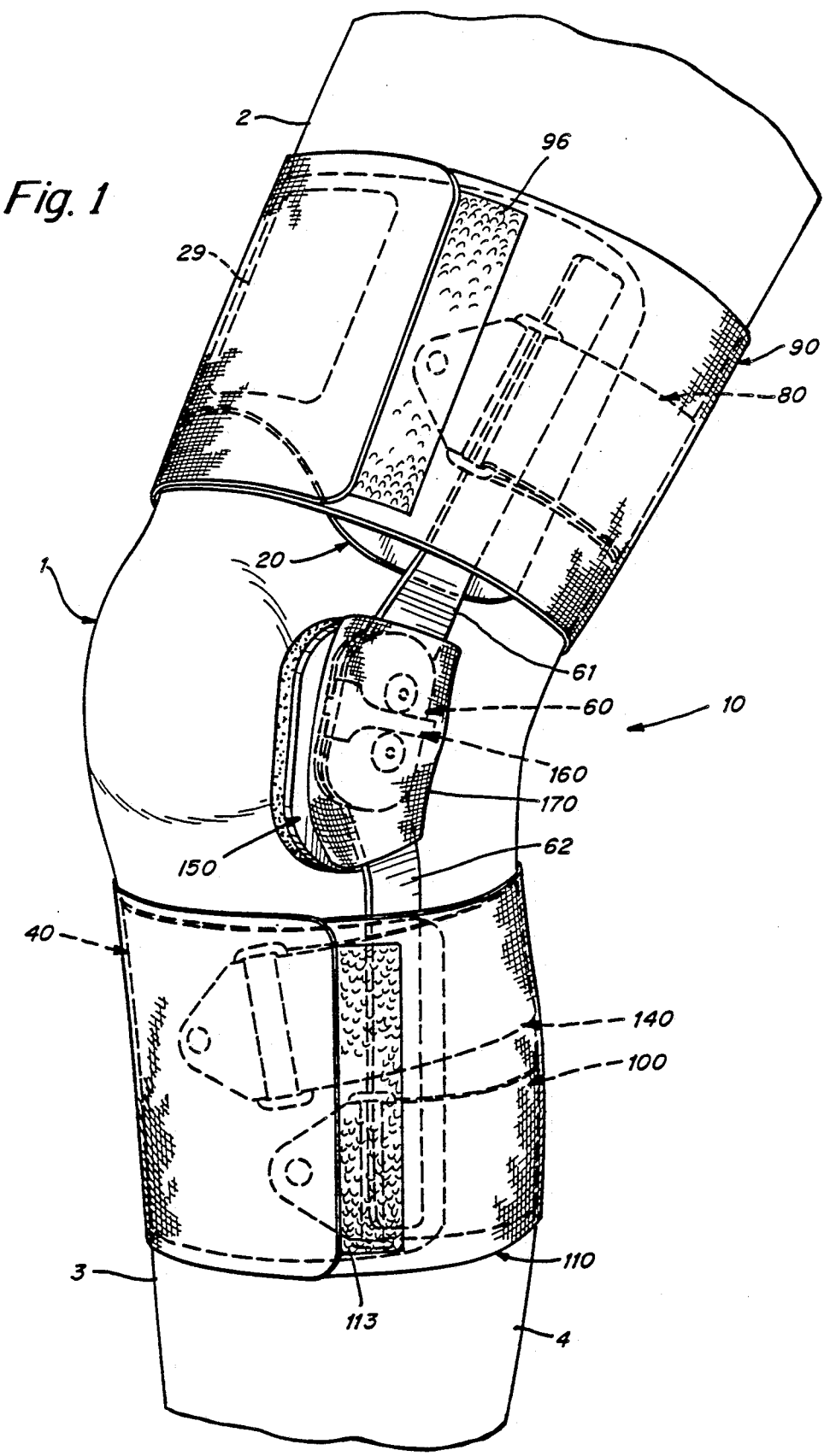
FIG. 1 is a lateral perspective view of a left knee and a first embodiment of the knee brace of this invention.

A first preferred embodiment of the knee brace of this invention is shown in FIGS. 1-7. The brace shown is designed for use on the left knee; a symmetrical version may be provided for use on the right knee.

As shown in FIGS.. 1-3, the brace includes an upper thigh cuff 20 secured to the leg above the knee by a non-stretchable upper cuff strap 80, and a lower shin cuff 40 secured to the leg below the knee by a non-stretchable lower cuff strap 100. On the lateral side of the brace, a polycentric hinge 60 is positioned at the lateral side of the knee with hinge arms or shafts 61, 62 connected to the thigh and shin cuffs, respectively. On the medial side of the brace, a medial plate 120 is positioned at the medial side of the knee which has an upper pivotal connection 33 to a lower flange 30 on thigh cuff 20 and two lower nonpivotal connections to the shin cuff 40 via a stretchable anterior strap 130 and a non-stretchable posterior strap 140. In addition, a pair of wide, stretchable, upper and lower outer bands 90, 110, respectively, are wrapped around the exterior of the brace at the thigh and calf.

Figure 5:
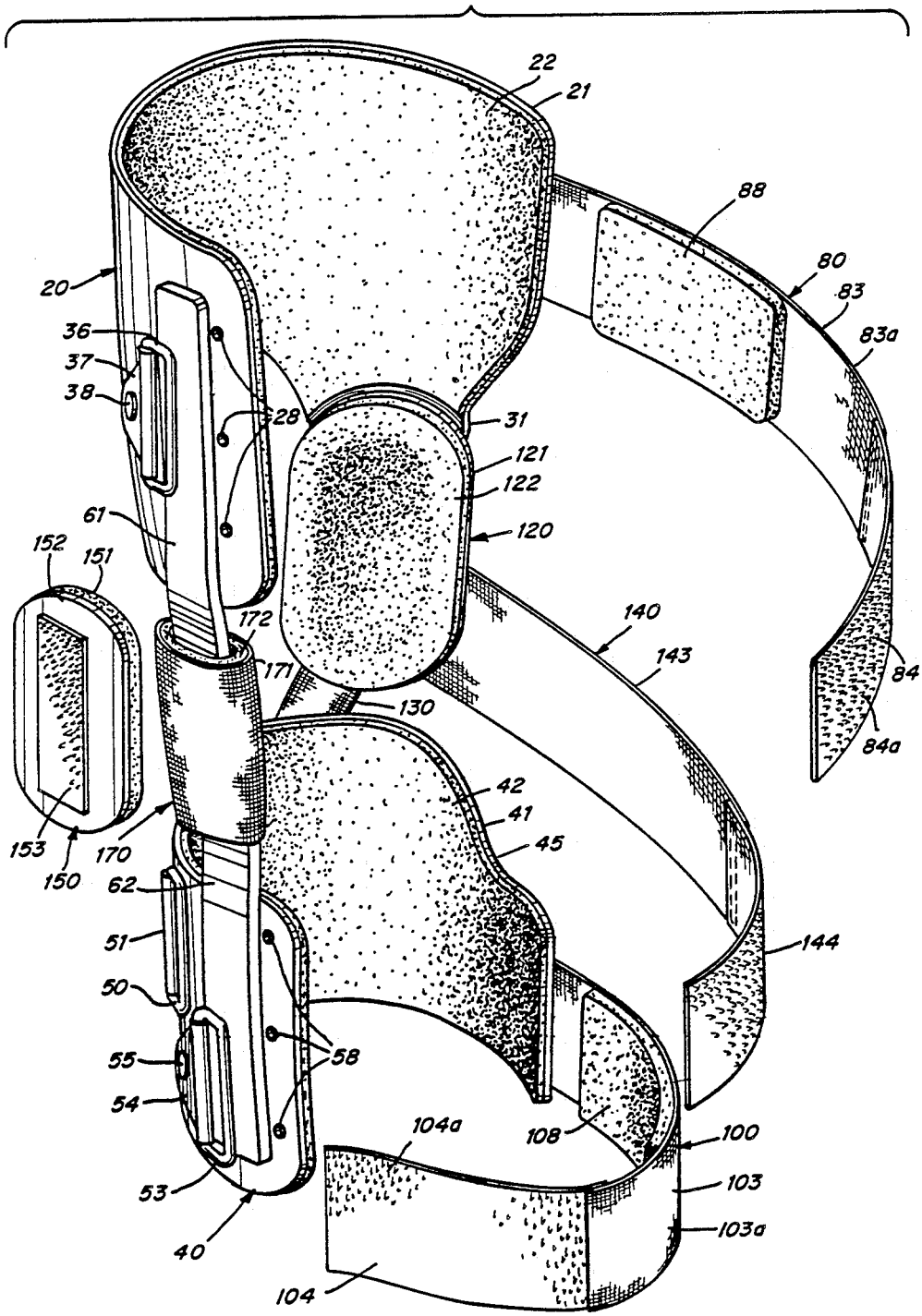
FIG. 5 is an exploded rear perspective view of the brace of FIG. 1 (without the outer thigh and calf bands).

An exploded perspective view of the various brace components, from the rear, is shown in FIG. 5.

Figure 2:
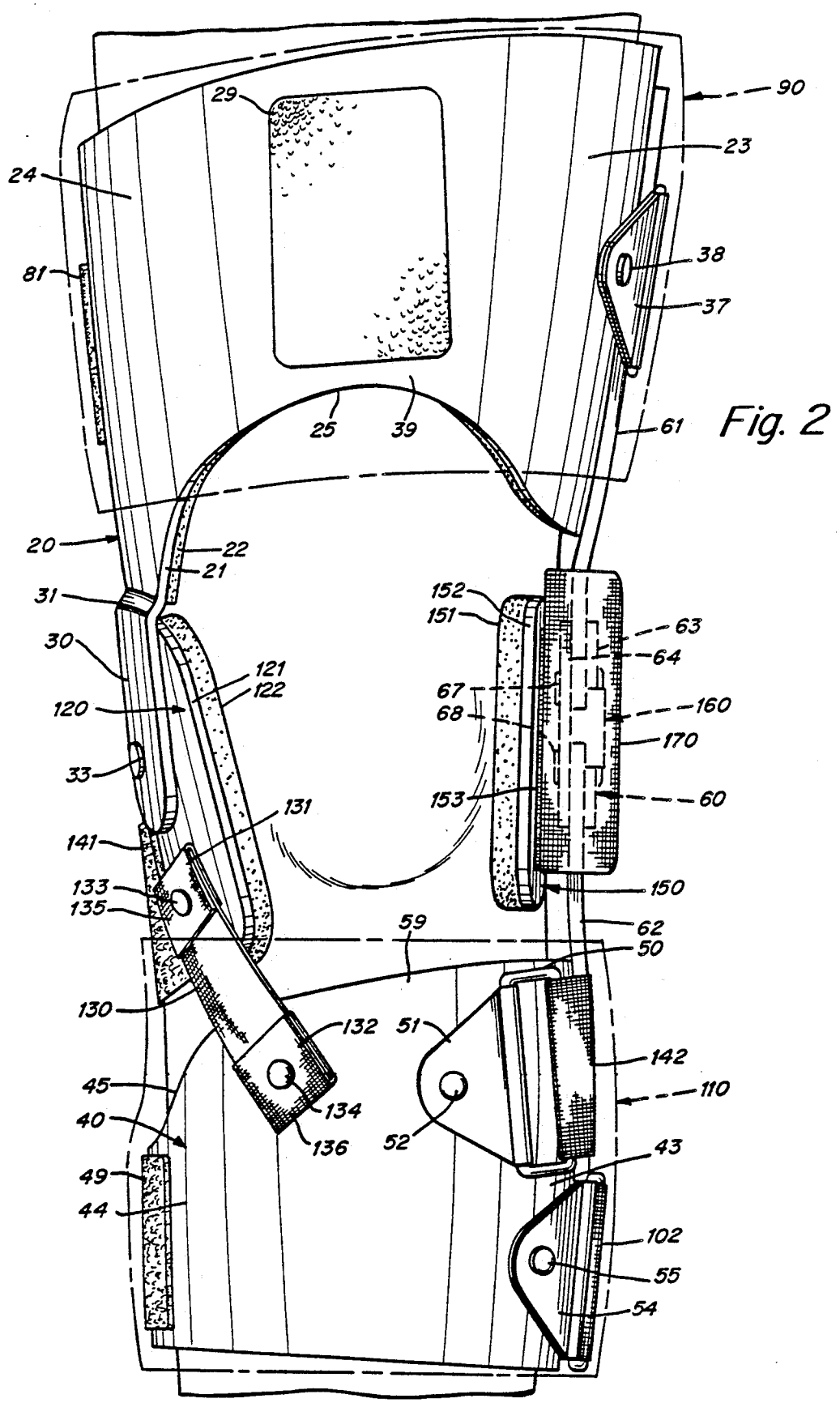
FIG. 2 is a front elevation view of the left knee and brace of FIG. 1 with the outer thigh and calf bands shown in phantom lines.
Figure 3:
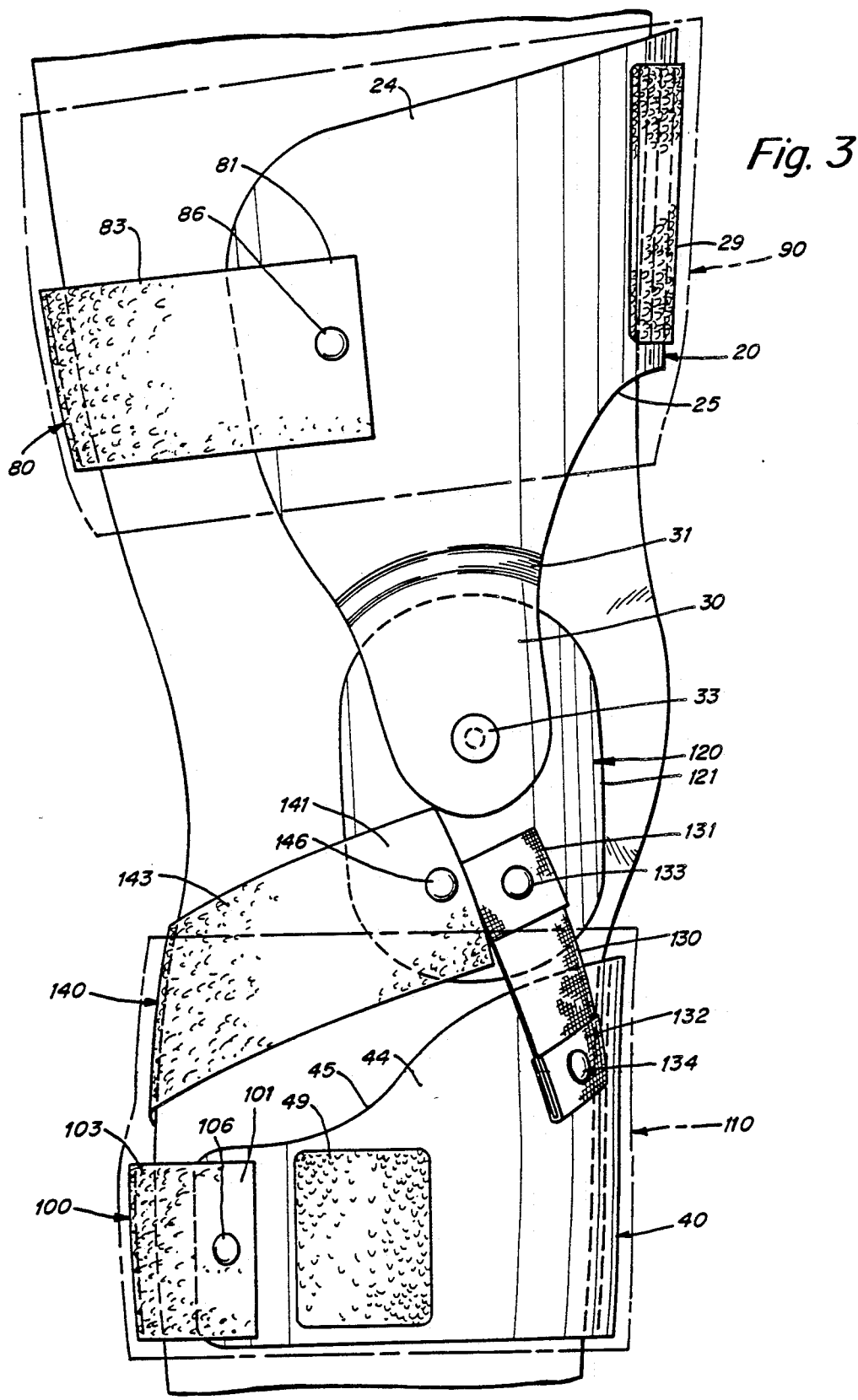
FIG. 3 is a medial elevation view of the left knee and brace of FIG. 1 with the outer thigh and calf bands shown in phantom lines.

As shown in FIGS. 1-3, the knee brace 10 is positionable on the thigh 2, shin 3 and calf 4 of the wearer for providing control of ligament instability to knee joint 1. Thigh cuff 20 has a hard outer shell 21 and a soft padded lining 22. Thigh cuff 20 is shaped to conform to the wearer's thigh and has an anterior portion 39 engaging the front (anterior) of the thigh and lateral and medial portions 23, 24 covering the lateral and medial sides of the thigh, respectively. The lower anterior edge 25 of the thigh cuff is curved upwardly to reduce the weight of the cuff and to prevent interference with the upper portion of the knee joint.

A non-stretchable upper cuff strap 80 extends behind the leg above the knee and releasably secures thigh cuff 20 to the leg via an adjustable fastener at one end. Upper strap 80 includes a medial portion 83 having VELCRO attachment loops 83a on its outer surface and padding 88 on its inner surface and a lateral portion 84 having VELCRO attachment hooks 84a on its outer surface (FIG. 5). Medial end 81 of upper cuff strap 80 is permanently attached to medial portion 24 of thigh cuff 20 by rivet 86 (FIG. 3). Lateral end 82 of thigh strap 80 is adjustably and releasably attached to lateral portion 23 of thigh plate 20 (see FIG. 4) by passing lateral portion 84 through ring 36 and folding back lateral portion 84 such that the hooks 84a engage the loops 83a on lateral portion 83. Ring 36 is permanently attached to lateral portion 23 of thigh cuff 20 by a plastic tab 37 having a channel through which one side of the ring passes and a rivet 38 which attaches tab 37 to thigh cuff 20.

Figure 4:
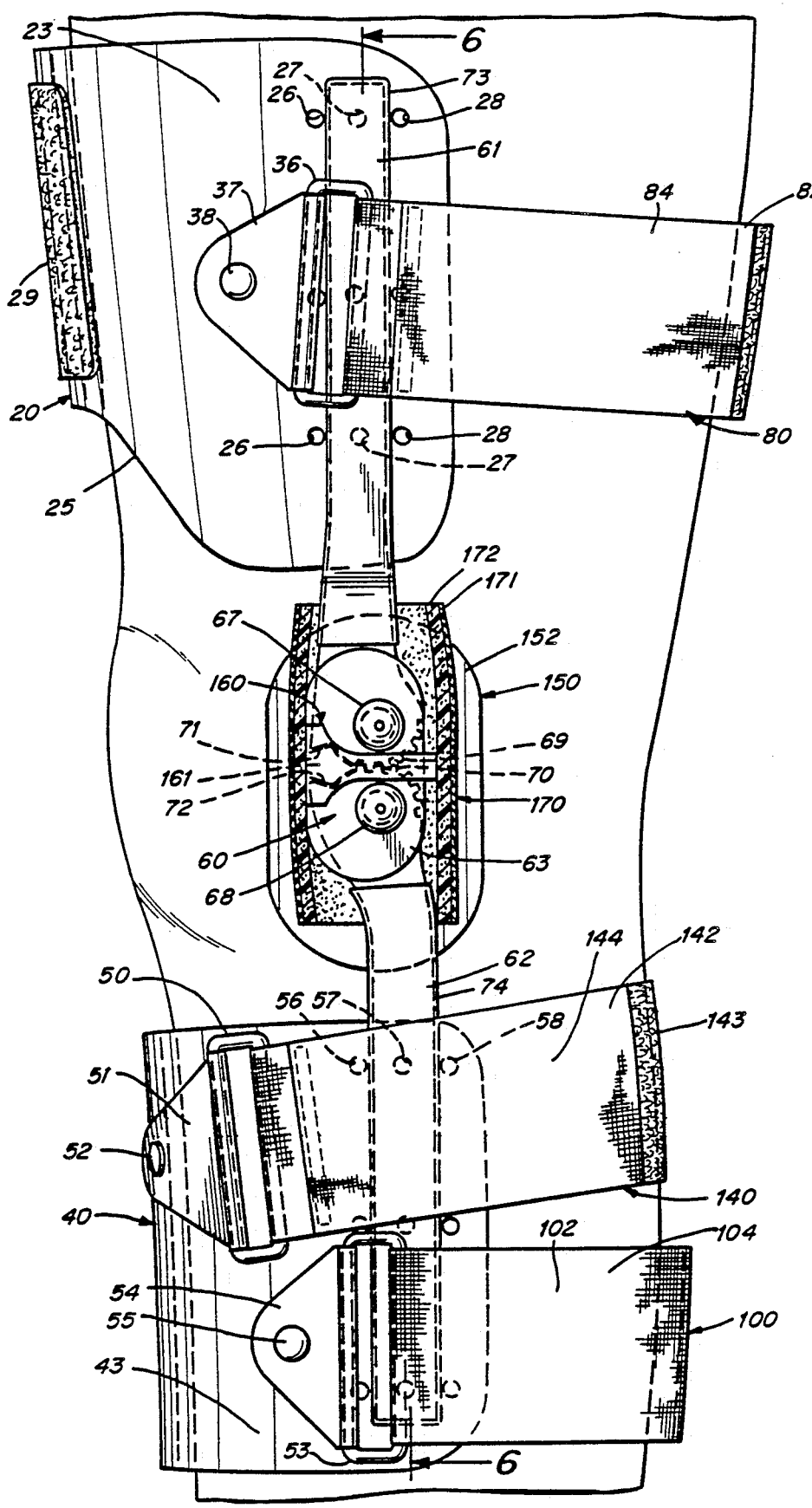
FIG. 4 is a lateral elevation view of the left knee and brace of FIG. 1 (without the outer thigh and calf bands).

Lower shin cuff 40 and lower cuff strap 100 function in much the same manner as the upper thigh cuff 20 and upper cuff strap 80. Thus, shin cuff 40 has a hard outer shell 41 and an inner padded lining 42. Shin cuff 40 includes anterior portion 59, lateral portion 43 and medial portion 44 which conform to the respective portions of the shin and calf. Non-stretchable lower cuff strap 100 includes a medial portion 103 having VELCRO attachment loops 103a on its outer surface and padding 108 on its inner surface, and a lateral portion 104 having VELCRO attachment hooks 104a on its outer surface (FIG. 5). A medial end 101 of strap 100 is permanently attached to medial portion 44 of shin cuff 40 by rivet 106 (FIG. 3). A lateral end 102 of strap 100 is adjustably and releasably attached to lateral portion 43 of shin cuff 40 by passing lateral end 102 through a ring 53 and doubling back onto itself such that the VELCRO attachment hooks 104a on lateral portion 104 engage the VELCRO attachment loops 103a on medial portion 103 (FIG. 4). A notch or cut-out 45 (FIG. 3) is provided along the upper edge of medial portion 44 to accomodate a non-stretchable posterior strap 140 as described hereinafter.

The non-stretchable upper and lower cuff straps 80, 100 extend approximately horizontally around the back of the leg and prevent the leg from backing out of the brace. Pads 88 and 108 are provided on the inner surfaces of the straps for comfort and to prevent chaffing of the leg.

To further stabilize the brace to the leg, a pair of wide, stretchable outer bands 90, 110 are provided in substantially horizontal alignment around the leg over the thigh and shin cuffs, and the cuff straps attached thereto (FIGS. 1-3). Upper band 90 has VELCRO attachment hooks at one end (not shown) for releasable attachment to VELCRO attachment loops 29 on an anterior portion 39 of thigh cuff 20 (FIG. 2). Thigh band 90 is then wrapped around the leg and secured at the other end by VELCRO attachment hooks (not shown) attachable to VELCRO attachment loops 96 on the outer surface of the band (FIG. 1). Similarly, lower band 110 is attached at one end with VELCRO attachment hooks to Velcro loops 49 on medial portion 44 of shin cuff 40 and is wrapped around the leg and secured at the other end by Velcro hooks to VELCRO attachment loops 113 on the outer surface of band 110 (FIG. 1).

The thigh and shin cuffs can be made as an off-the-shelf item in different sizes, e.g., small, medium and large. Within each cuff size, differences in girth are accomodated by providing medial-lateral flexibility to the cuff and adjustability to the cuff strap. Furthermore, three sets of vertically aligned apertures are provided on the cuffs for adjustably connecting the lateral hinge thereto, as described hereinafter.

The outer shells 21, 41 of the thigh and shin cuffs are preferably a hard, substantially rigid, molded shell of a polyethylene-polypropylene copolymer, about 3/16" in thickness, which have some medial-lateral flexibility to accomodate legs of varying girth. The shell is impact-resistant and preferably is made of a plastic such as polyethylene or polypropylene, and more preferably a copolymer thereof. Each shell has a $\frac{1}{4}$" inch foam liner 22, 42 for comfort, for accomodating differences in leg girth, and for suspension (i.e., holding up the brace so it does not slip down on the leg). The lining is a softer, less abrasive material than the shell and preferably is a polyethylene foam sold under the trademark Evazote by Bakelite Xylonite Limited, London, England. The shell is preferably prefabricated from standard molds. The foam liner is applied to the inner surface of the shell by adhesive or by heat bonding.

The upper and lower cuff straps 80, 100 are each 2" wide and are made of two sections of Dacron sewn together end-to-end. The sections have either VELCRO attachment hooks or loops on one side thereof. The medial ends of the straps are folded back for reinforcement before attaching the straps with metal rivets to the cuffs. The rings 36, 53 by which the straps are adjustably attached to the cuffs at their lateral ends are 2¼" wide metal D-rings. The plastic tabs 37, 54 are double thickness for strength and are attached via metal rivets 38, 55 to the cuffs. The padding sections 88, 108 are about ⅛" thick foam rubber pads and are adhesively bonded to the inner surfaces of strap sections 83, 103. The outer bands 90, 110 are about 4" wide and are made of neoprene rubber sold by Rubatex, of Bedford, Va.

Figure 6:
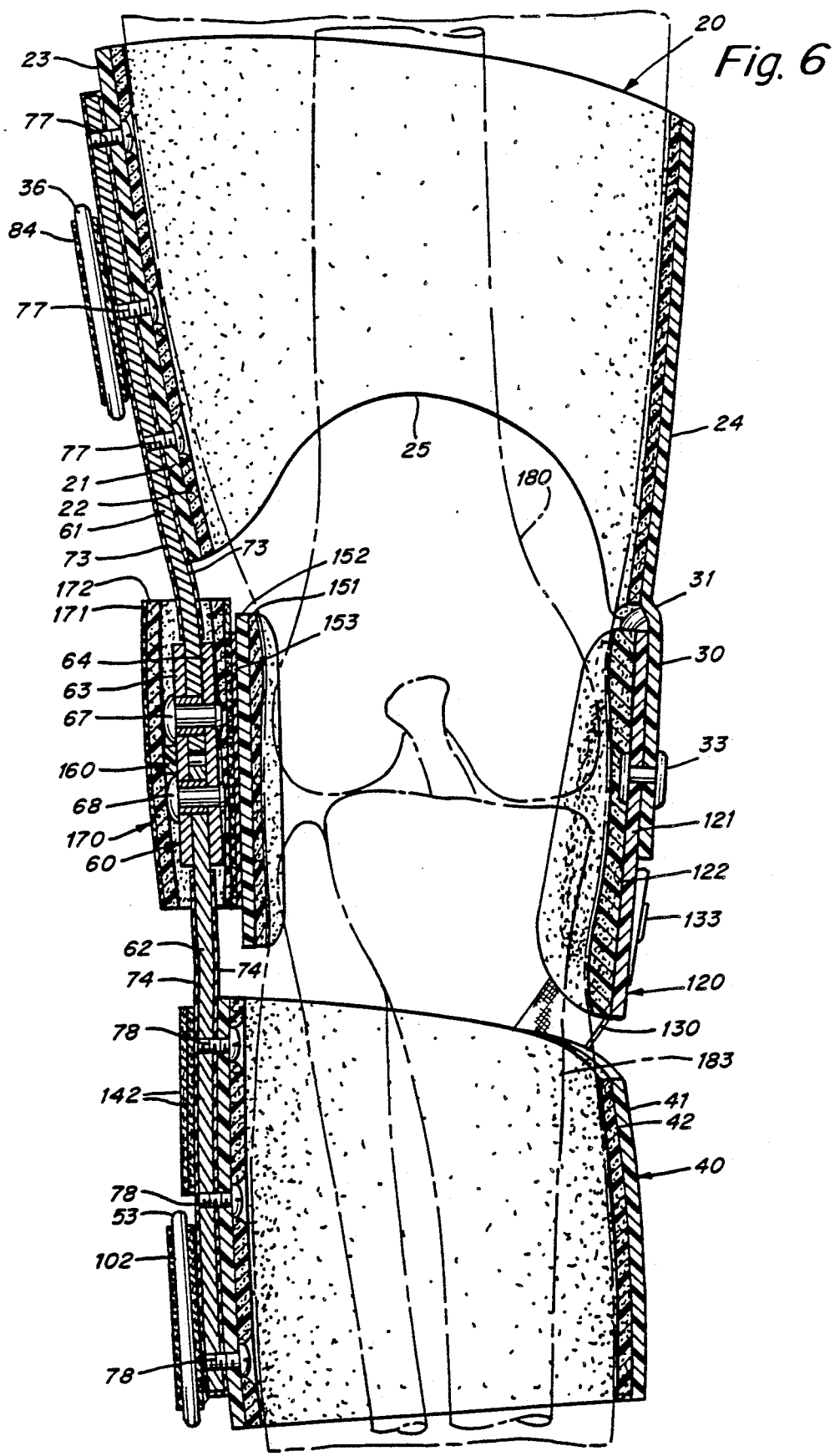
FIG. 6 is a cross sectional view taken along the section lines 6—6 of FIG. 4 showing the leg bones at the knee joint and the anterior cruciate ligament in phantom lines.

As best shown in FIGS. 2, 4 and 6, a polycentric hinge 60 is provided on the lateral side of the knee extending between and connecting lateral portions of the shin and thigh cuffs. The hinge has two pivot points 67, 68 and a pair of shafts or arms 61, 62 extending above and below the pivot points. A pair of spaced-apart outer and inner connecting plates 63, 64 have pairs of aligned apertures through which pins 67, 68 pass to define the pivot points. The upper end of lower shaft 62 is positioned between connecting plates 63, 64 and has an aligned aperture through which lower pivot pin 68 passes. The lower end the lower shaft 62 is attached at three vertically spaced points to the lateral portion 43 of the shin cuff by threaded screws 78 which pass through aligned apertures 56, 57, or 58 in the shaft and cuff (FIG. 6). Similarly, the lower end of the upper shaft 61 is positioned between connecting plates 63, 64 and has an aligned aperture through which upper pivot pin 67 passes. The upper end of upper shaft 61 is attached to the lateral portion 23 of thigh cuff 20 by three threaded screws 77 which pass through aligned apertures 26, 27, 28 in the shaft and cuff (FIG. 6). The shafts 61, 62 are preferably 8" in length to provide substantial leverage and are made of a high-strength, light-weight alloy. The shafts 61, 62 pivot around their respective pivot points 67, 68 and have intermeshing gear teeth 69, 70 at their mating ends so as to cause simultaneous pivotal action of both shafts about their pivotal connections with the plates. The shafts maintain the vertical alignment of the femur 180 and tibia 183 (FIGS. 6-7), prevent excessive rotation of the tibia with respect to the femur, and permit substantially natural flexion and extension of the knee. Preferably, a non-abrasive polymeric coating 73, 74 is provided on the upper and lower shafts to prevent injury. The polycentric hinge is fully described in U.S. Pat. No. 4,633,867 to Kausek et al. which is hereby incorporated by reference. Preferably, an extension stop 160 (FIGS. 2 and 4) is provided for limiting the forward pivotal rotation of the shafts, as described in U.S. Pat. No. 4,732,143 to Kausek et al., which is hereby incorporated by reference. Flanges 71, 72 on the ends of shafts 61, 62 adjacent the gear teeth engage an extension block 161 for preventing the knee from pivoting forwardly beyond the maximum desired articulation, i.e., preventing hyperextension.

The central portion of hinge 60 is encased by a padded tubular sleeve 170, having an inner padding 172 and outer elastomeric covering 171, which prevents chaffing against the knee and injury to articles which it may contact. Sleeve 170 also allows attachment of a lateral plate as described hereinafter. The sleeve may be made of rubber or neoprene. The outer surface of the sleeve has a loop material which acts as VELCRO attachment loops for the releasable attachment of the lateral plate.

The lateral plate 150 is designed to engage the lateral side of the knee so as to anchor the brace on the knee and control ligament instability. Plate 150 includes a hard and substantially rigid outer shell, 152 and an inner soft pad 151 of a non-abrasive, resilient material which is shaped to conform to the tibial and femoral condyles at the lateral side of the knee. VELCRO attachment hooks 153 are attached to the back of the shell for releasable attachment to the hinge cover 170. Alternatively, the lateral plate 150 may be affixed by adhesive or rivets to the inner hinge plate 64 and the sleeve 170 applied over the hinge and lateral plate.

At the medial side of the knee, as shown in FIGS. 2, 3, 5 and 6, there is provided a medial articulation plate 120. Plate 120 is designed to engage the tibial and femoral condyles at the medial side of the knee so as to stabilize the brace and provide a medial point of articulation. Medial plate 120 has a hard, substantially rigid outer shell 121 and an inner lining 122 of a non-abrasive, resilient material which is shaped to conform to the medial knee joint. The plate 120 has three points of attachment, defined by an upper pivot pin 33 and two lower rivets 133 and 146. A medial flange 30 extends downwardly from medial portion 24 of thigh cuff 20 and over the outer surface of plate 120 via outwardly curved shoulder 31 (FIG. 2). A rigid plastic pivot pin 33 extends through aligned apertures in medial flange 30 and medial plate 120 for pivotally connecting the same. The vertical position of the medial pivot pin 33 is between and preferably at about the mid-point between the pivot pins 67, 68 of the lateral hinge. The outer shells 152, 121 of the lateral and medial condylar plates are made of the same material and thickness as the cuffs 20, 40. The inner pads, 151, 122 are preferably about ⅜" thick and made of a polymer foam such as foam rubber. Preferably, medial plate 120 is an elongated oval about 4¼" in length and 3" in width and the shell and padding are slightly concave (inwardly).

A stretchable anterior strap 130 is non-pivotally and permanently attached at its upper end 131 to a lower, anterior attachment point on medial plate 120 by metal rivet 133. Strap 130 then extends anteriorly and downwardly at an angle of about 45° and is non-pivotally attached at its lower end 132 to the anterior portion 59 of shin cuff 40 by metal rivet 134. Anterior strap 130 allows limited vertical separation of the medial plate 120 and shin cuff 40 during knee flexion to prevent the shin cuff from riding up on the leg. Furthermore, in conjunction with a posterior strap 140 described hereinafter, it prevents the lower end of medial plate 120 from pivoting forwardly and thus restrains anterior movement of the tibia with respect to the femur. As shown, front medial strap 130 is about 3.25" in length and is made of a cotton-covered elastic. Fabric reinforcements 135, 136 made of nylon are provided at each end of the strap for more secure attachment to the lower cuff and medial plate.

A non-stretchable posterior strap 140 is provided between medial plate 120 and shin cuff 40 to restrain forward movement of the lower end of medial plate 120 as it pivots about pin 33 during flexion of the knee. Medial end 141 of strap 140 is permanently and non-pivotally attached by metal rivet 146 to a lower, posterior attachment point on medial plate 120. Strap 140 includes medial portion 143 having VELCRO attachment loops on its outer surface and lateral portion 144 having VELCRO attachment hooks on its outer surface (FIG. 5). Strap 140 extends behind the back of the leg and is adjustably and releasably secured to the lateral portion of the shin cuff by metal D-ring 50 which is attached by plastic tab 51 and metal rivet 52 to shin cuff 40. The lateral end 142 of strap 140 is passed through the D-ring and pulled back on itself for attaching VELCRO attachment hooks on section 144 to VELCRO attachment loops on section 143. Strap 140 is preferably of the same construction as the cuff straps 80, 100.

Figure 7:
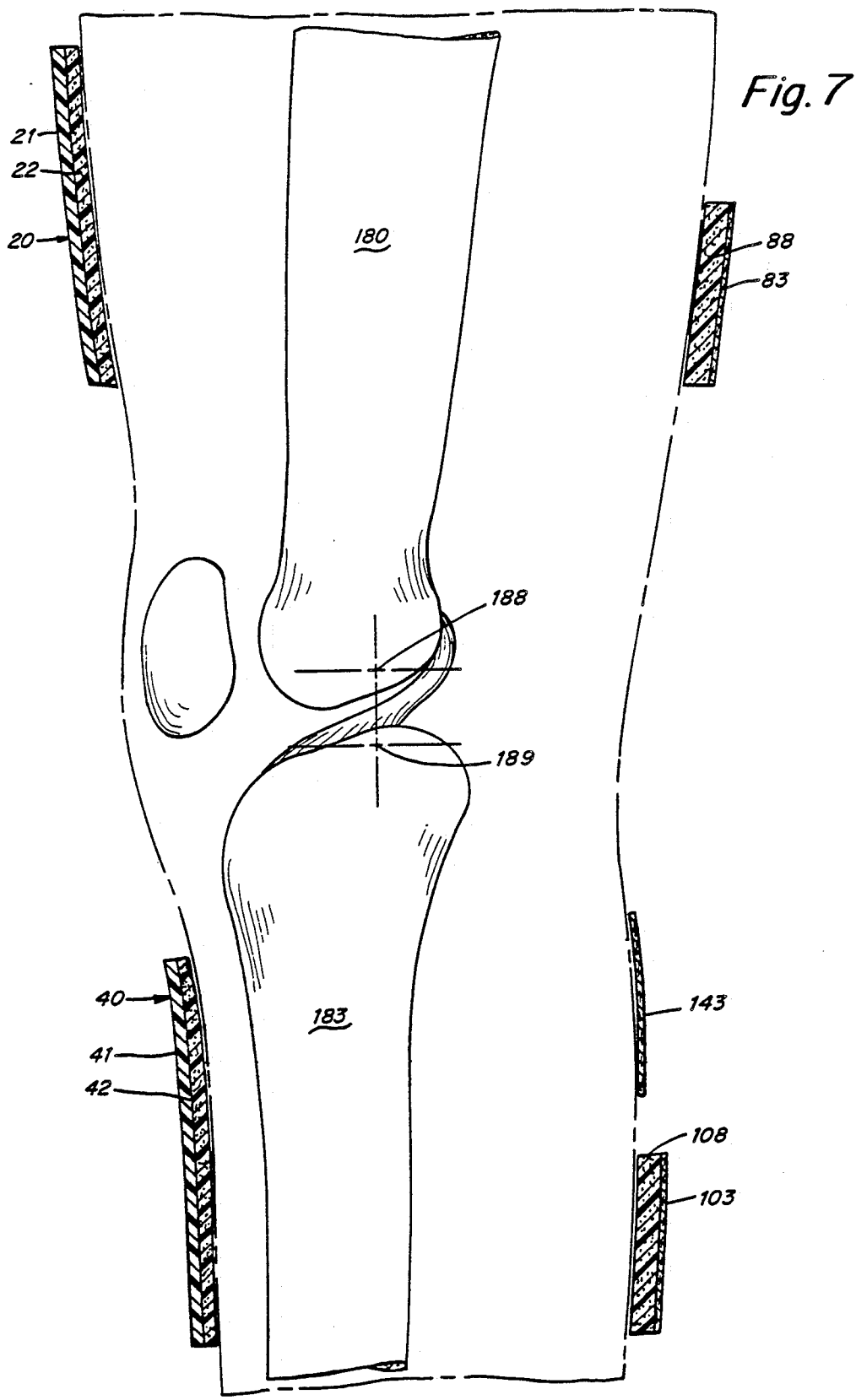
FIG. 7 is a schematic view of the lateral side of the left knee showing the anterior cruciate ligament and the two pivot points of the polycentric hinge.
Figure 8:
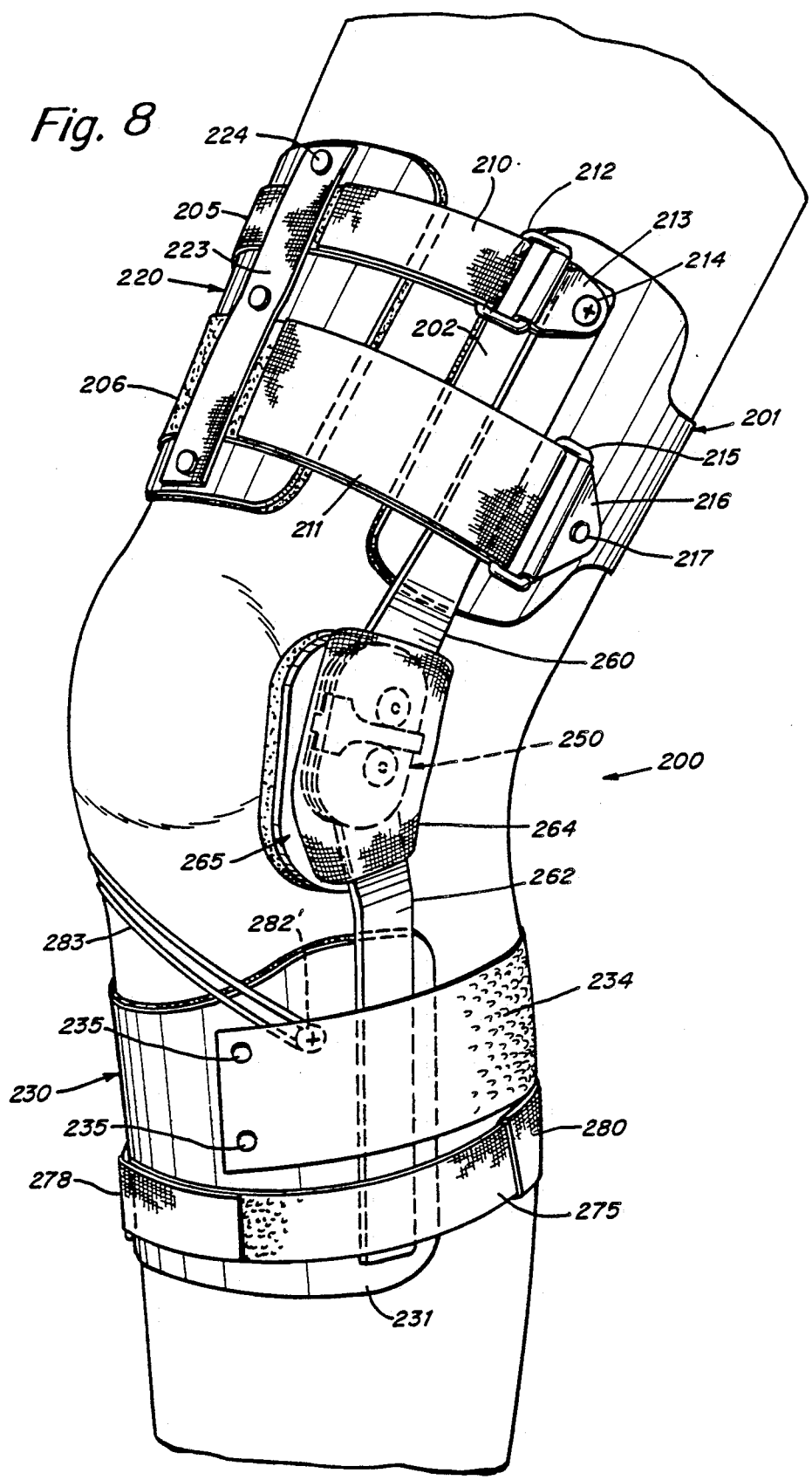
FIG. 8 is a lateral perspective view of a second embodiment of the knee brace of this invention.
Figure 9:
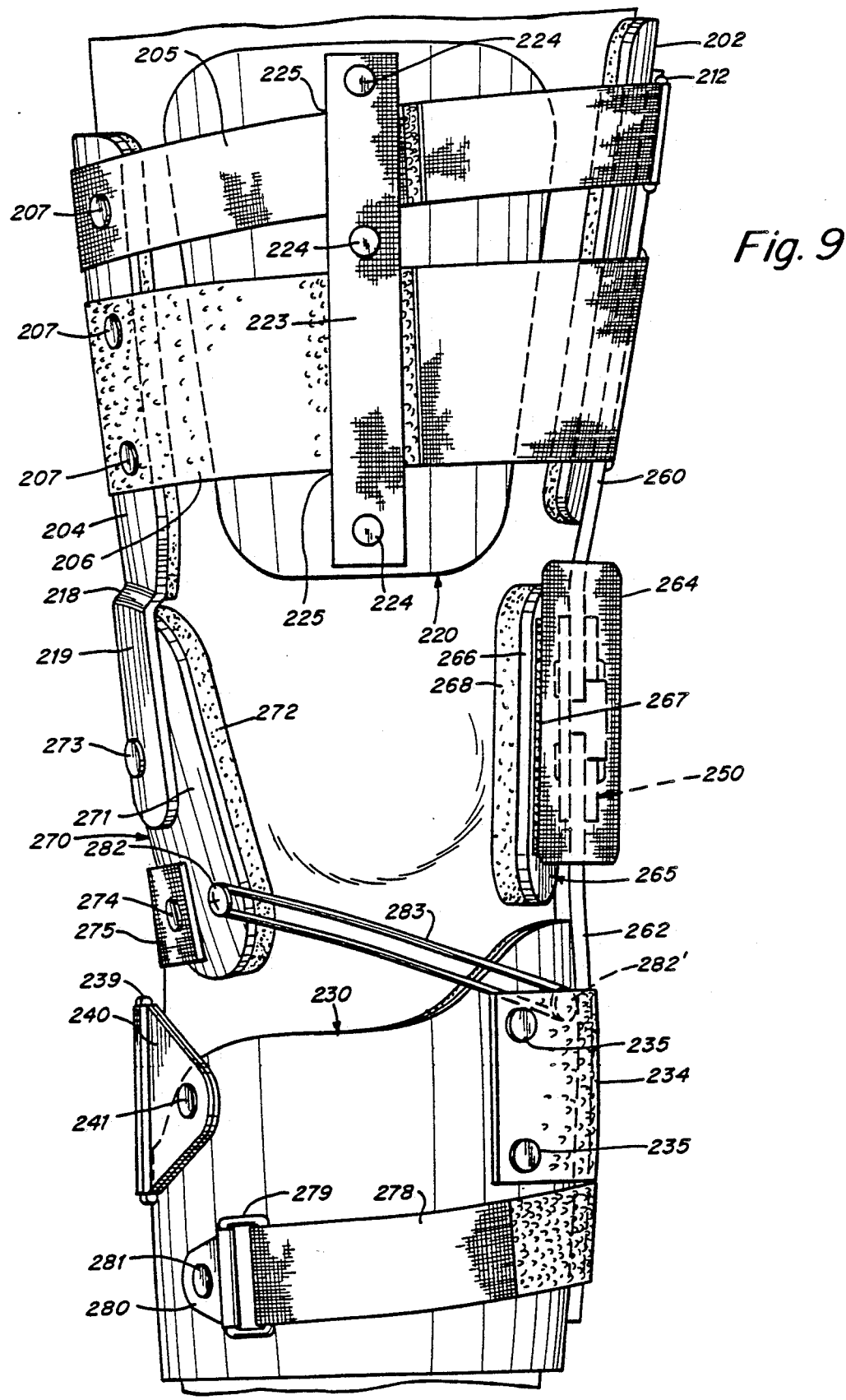
FIG. 9 is a front elevation view of the knee brace of FIG. 8.
Figure 10:
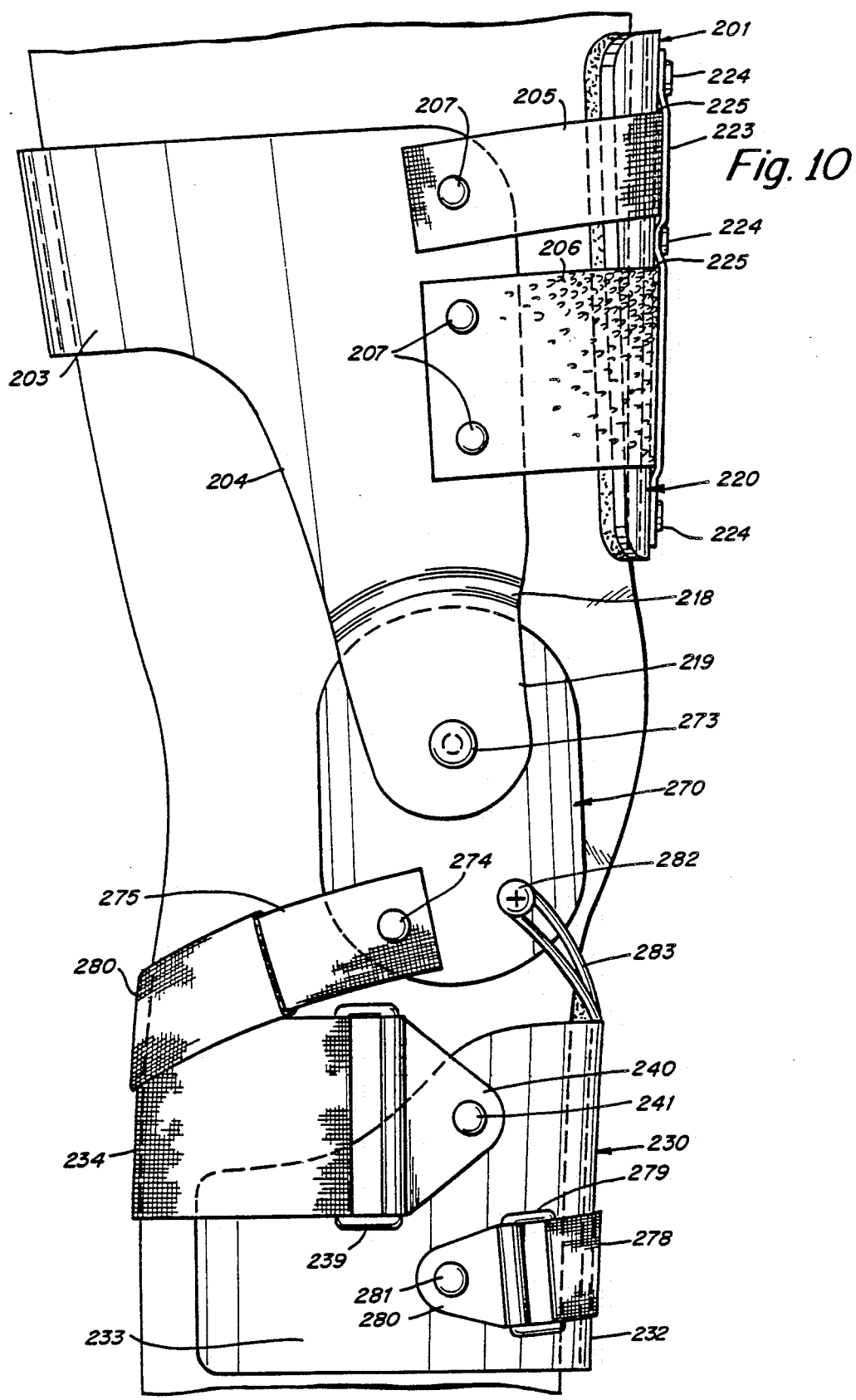
FIG. 10 is a medial elevation view of the knee brace of FIG. 8.
Figure 11:
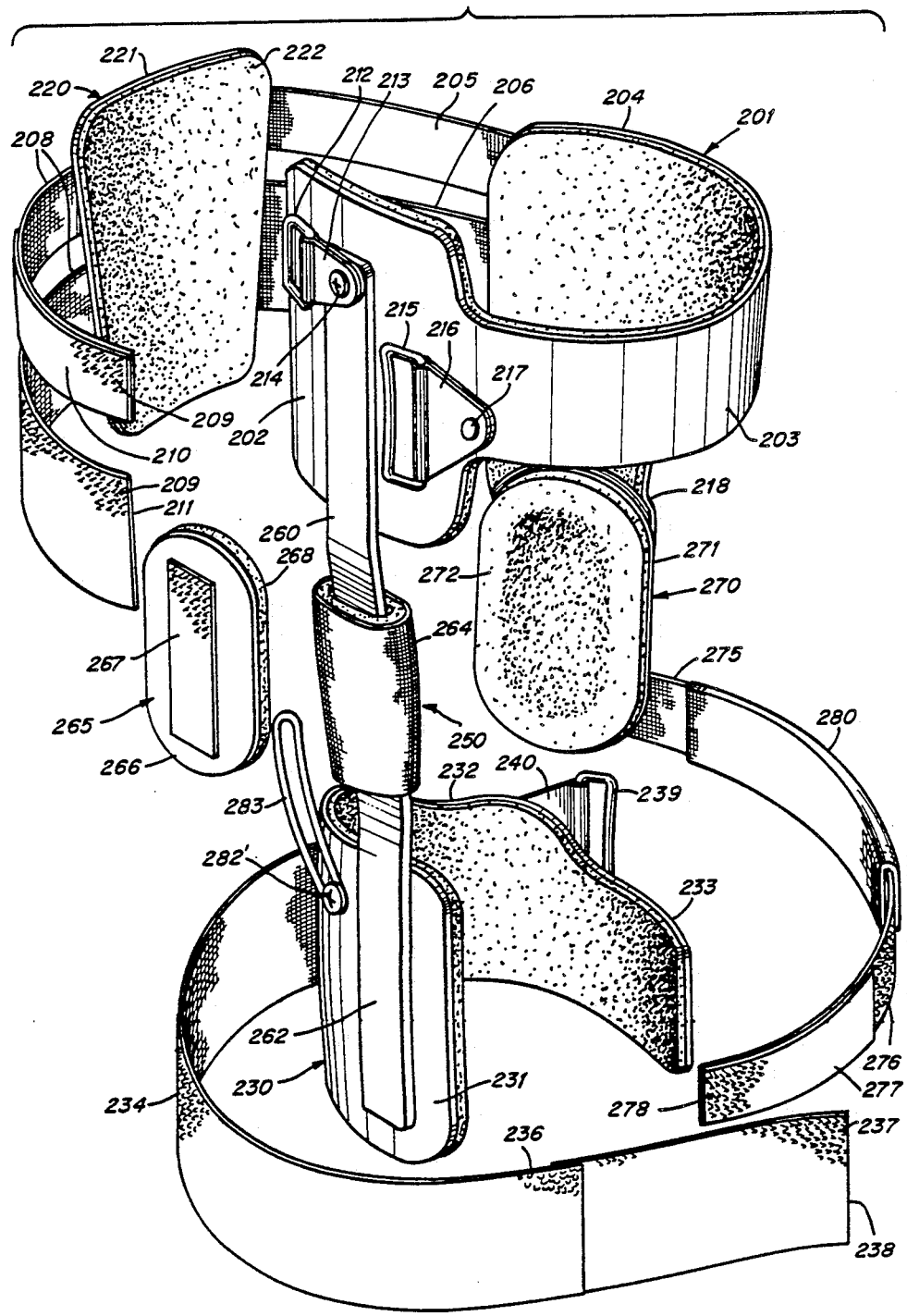
FIG. 11 is an exploded rear perspective view showing the various components of the knee brace of FIG. 8.

The anterior and posterior straps 130, 140 unify the thigh and shin cuffs at the medial side of the brace without the use of a second polycentric hinge. They also affix the medial plate to the knee to provide a medial point of articulation. The lateral polycentric hinge 60 approximates the two pivot points of the natural knee, as shown in FIG. 7 at 188 and 189.

A second embodiment of the invention is shown in FIGS. 8-11. In the second embodiment the upper cuff engages the back of the thigh, as compared to the first embodiment wherein the upper cuff engages the front of the thigh. The second embodiment functions in substantially the same manner as the first embodiment and thus will be described with less detail.

The knee brace 200 of the second embodiment includes an upper cuff 201 having a lateral portion 202, posterior portion 203, and medial portion 204. A pair of non-stretchable upper cuff straps 205, 206 are attached by rivets 207 to medial portion 204 and are wrapped in parallel alignment around the front of the thigh. Upper cuff straps 205, 206 have VELCRO attachment loops 208 on their outer surfaces and Velcro hooks 209 on the outer surfaces of distal end portions 210 and 211. Distal end 210 of strap 205 is releasably and adjustably secured by passing through ring 212 attached by tab 213 and rivet 214 to an upper hinge arm 260 attached to lateral portion 202 of upper cuff 201. Distal end 210 is then folded back onto strap 205 such that hooks 209 engage loops 208. In a similar manner, distal end 211 of strap 206 passes through ring 215 which is attached by tab 216 and rivet 217 to lateral portion 202 of cuff 201.

A thigh plate 220 having a hard outer shell 221 and soft lining 222 is positionable on the front of the thigh and shaped to conform thereto. A vertically disposed nylon strip 223 is attached by metal rivets 224 at three vertically spaced points to the outer shell 221 of thigh plate 220. A pair of channels 225 are defined between strip 223 and plate 220 between adjacent pairs of rivets 224 through which upper cuff straps 205, 206 pass for positioning thigh plate 220 on the front of the thigh. Channels 225 may be somewhat wider than straps 205, 206 to allow some vertical adjustability of thigh plate 220 on the thigh.

Knee brace 200 further includes a lower cuff 230 having a lateral portion 231, anterior portion 232, and medial portion 233. A non-stretchable lower cuff strap 234 is attached at one end by a pair of rivets 235 to anterior portion 232 of lower cuff 230. Strap 234 has VELCRO attachment loops 236 on its outer surface and a distal end portion 238 having VELCRO attachment hooks 237 on its outer surface. Strap 234 is wrapped around the back of the leg and is adjustably and releasably connected by passing distal end 238 through ring 239 which is attached by tab 240 and rivet 241 to medial portion 233 of lower cuff 230. Distal end 238 is then folded back such that VELCRO attachment hooks 237 engage VELCRO attachment loops 236.

A polycentric hinge 250 is disposed at the lateral side of the knee. Hinge 250 is identical to hinge 60 of the first embodiment and will therefore not be described in detail. Hinge 250 includes an upper arm 260 attached by three vertically aligned rivets (not shown) to lateral portion 202 of upper cuff 201 and has a lower arm 262 which is attached by three vertically aligned rivets (not shown) to lateral portion 231 of lower cuff 230. Hinge 250 has a tubular sleeve 264 covering the central hinge portion. Sleeve 264 has VELCRO attachment loops on its outer surface for attachment to VELCRO attachment hooks 267 on lateral plate 165. Plate 265 has an outer shell 266 and a softer lining 268 shaped to conform to the lateral side of the knee.

Knee brace 200 further includes a medial plate 270 having an outer shell 271 and a softer lining 272 shaped to conform to the medial side of the knee. A lower flange 219 extending from medial portion 204 of upper cuff 200 is offset outwardly of medial portion 204 by shoulder 218 so that flange 219 lies over the outer surface of medial plate 270. Similar to the medial plate of the first embodiment, an upper pivot point 273 connects the flange 219 and plate 270 and a lower posterior rivet 274 connects one end of a non-stretchable posterior strap 275 to medial plate 270. Strap 275 is wrapped around the back of the calf and is connected at its opposite end to lower cuff 230. Strap 275 has loops 276 on its outer surface and VELCRO attachment hooks 277 on a distal end portion 278. Distal end 278 passes through ring 279 which is attached by tab 280 and rivet 281 to anterior portion 232 of lower cuff 230. End 278 is folded back so that hooks 277 engage loops 276. A pad 280 is provided on a central portion of shaft 275 to prevent chaffing against the back of the leg.

An anterior lower attachment point between medial plate 270 and lower cuff 230 is defined by post or screw 282 on the outer shell 271 of plate 70. A second post or screw 282' is provided on the anterior portion 232 of lower cuff 230. A stretchable band or strap 283 forms a closed loop with opposite ends disposed around posts 282 and 282'. Strap 283 functions in a manner similar to strap 130 of the first embodiment.

A third embodiment of the invention is shown in FIGS. 12–17. A number of the components in the third embodiment are the same or substantially the same as components in the first and second embodiments and thus will be described with less detail.

Figure 17:
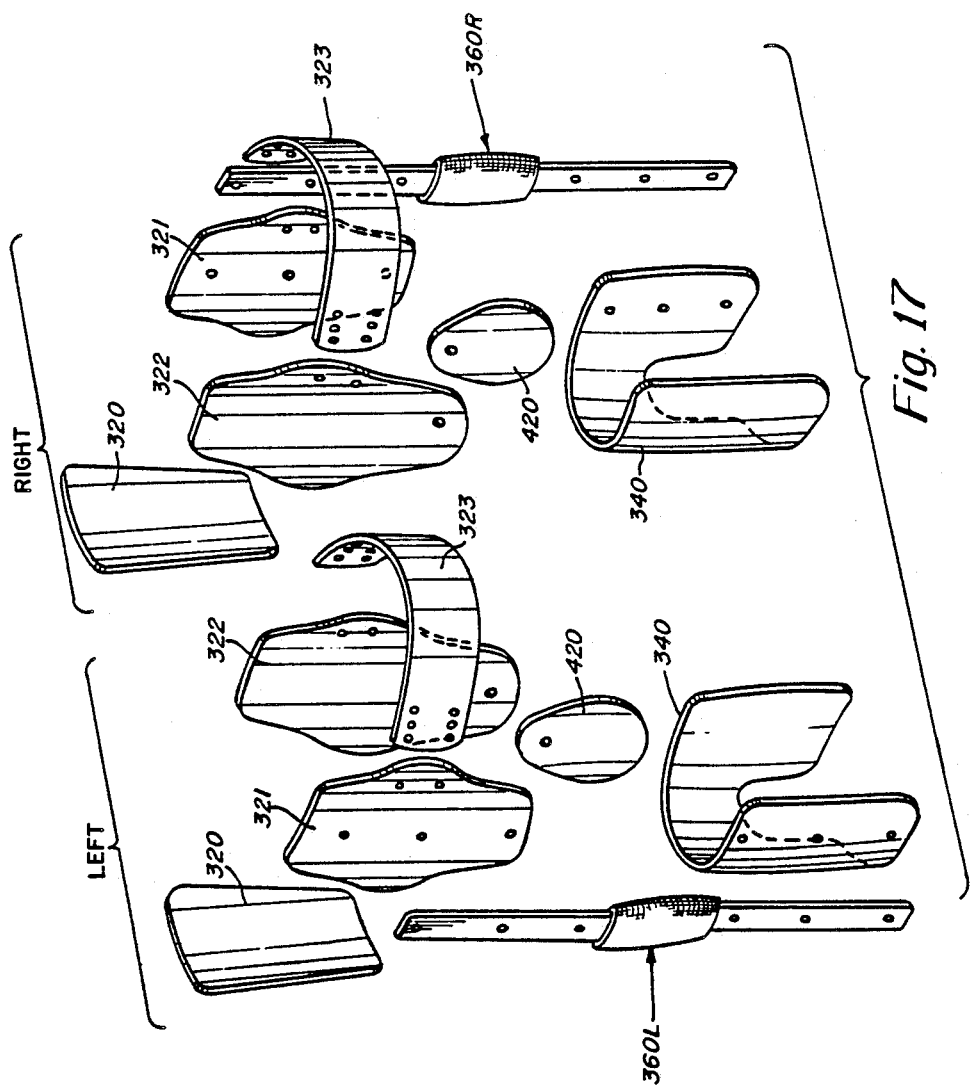
FIG. 17 is an exploded rear perspective view showing certain components of left and right knee braces and the interchangability of these components.

The knee brace 310 of the third embodiment includes four separate thigh plates, a medial articulation plate, and a shin cuff which are interchangeable for use on the left and right legs, as shown in FIG. 17. The four thigh plates include an anterior thigh plate 320, a lateral thigh plate 321, a medial thigh plate 322, and a posterior thigh plate 323, each consisting of an outer hard and rigid shell 324 and an inner soft lining 325. Each of the thigh plates is arcuately shaped to conform to the thigh. The lateral thigh plate has flared side edges 329 and the medial thigh plate has flared side edges 330 to increase the gripping action of the medial and lateral plates on the thigh.

Figure 13:
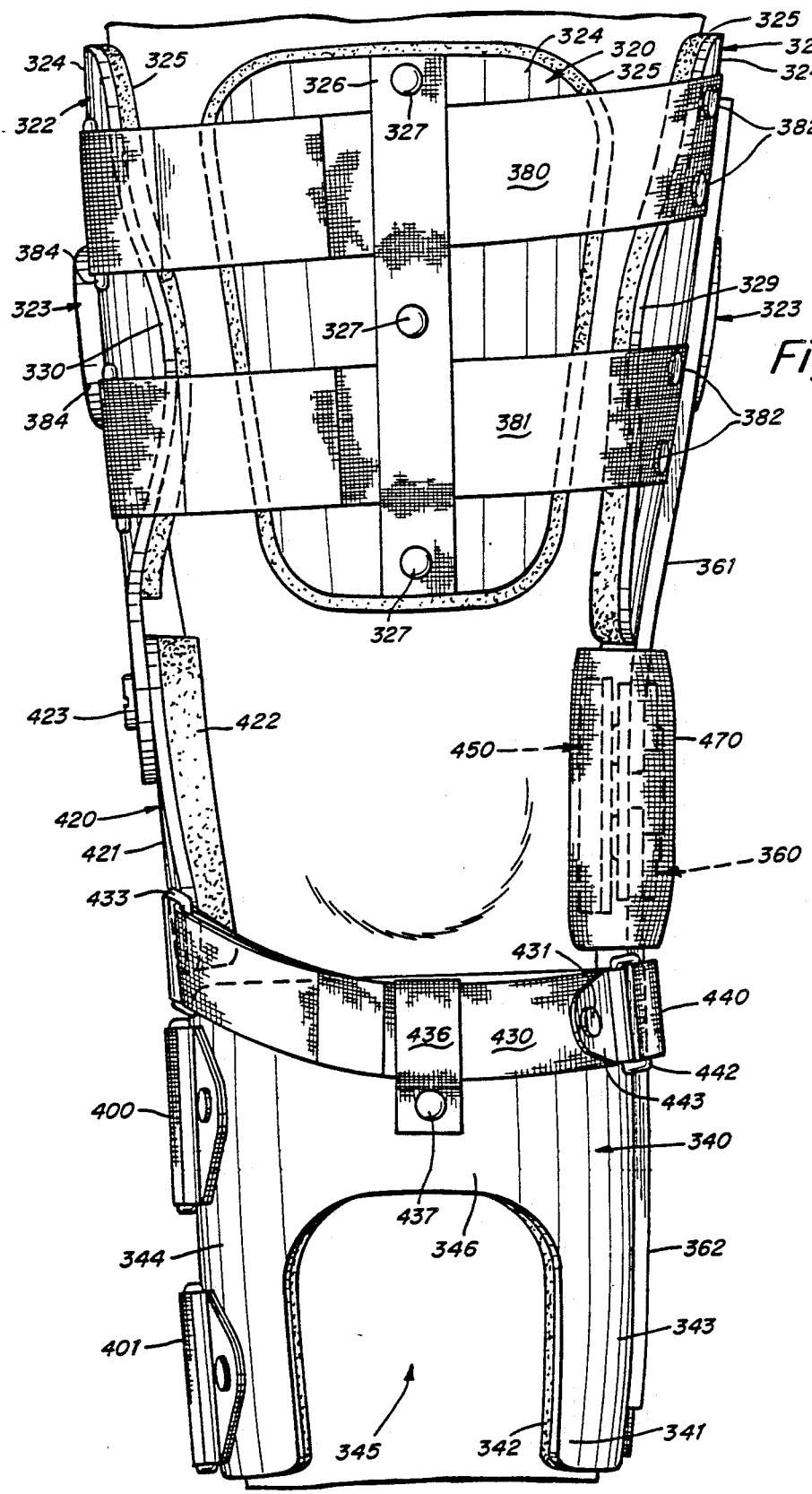
FIG. 13 is a front elevation view of the knee brace of FIG. 12.
Figure 14:
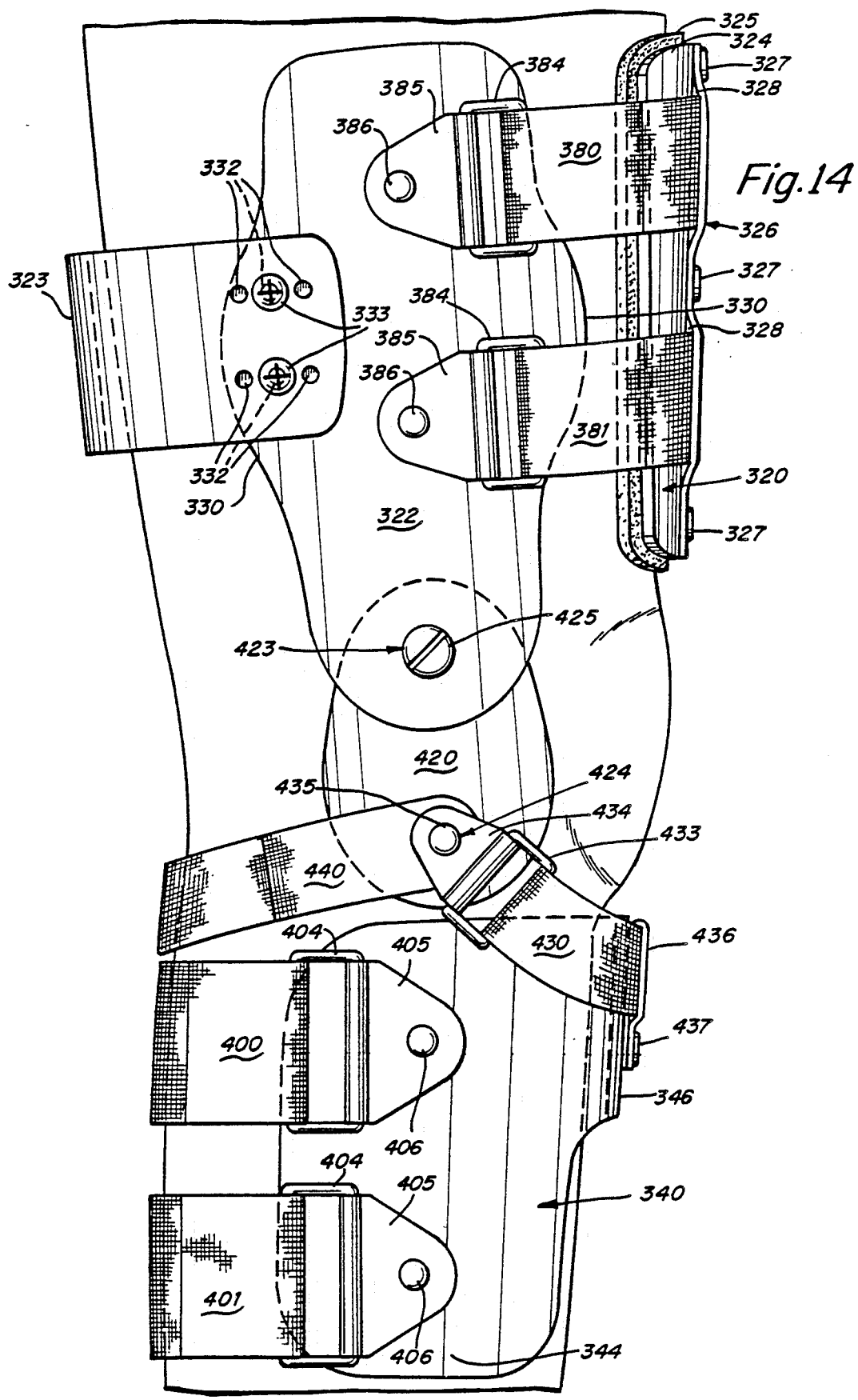
FIG. 14 is a medial elevation view of the knee brace of FIG. 12.

As shown in FIGS. 13–14, a vertically disposed flexible strap 326 is attached by metal rivets 327 at three vertically spaced points to the outer shell 324 of anterior thigh plate 320. A pair of channels 328 are defined between strap 326 and plate 320 between adjacent pairs of rivets 327 through which upper and lower thigh straps 380 and 381 respectively pass for positioning the anterior thigh plate 320 on the front of the thigh. Channels 328 may be somewhat wider than straps 380, 381 to allow some vertical adjustability of anterior thigh plate 320 on the thigh.

Figure 12:
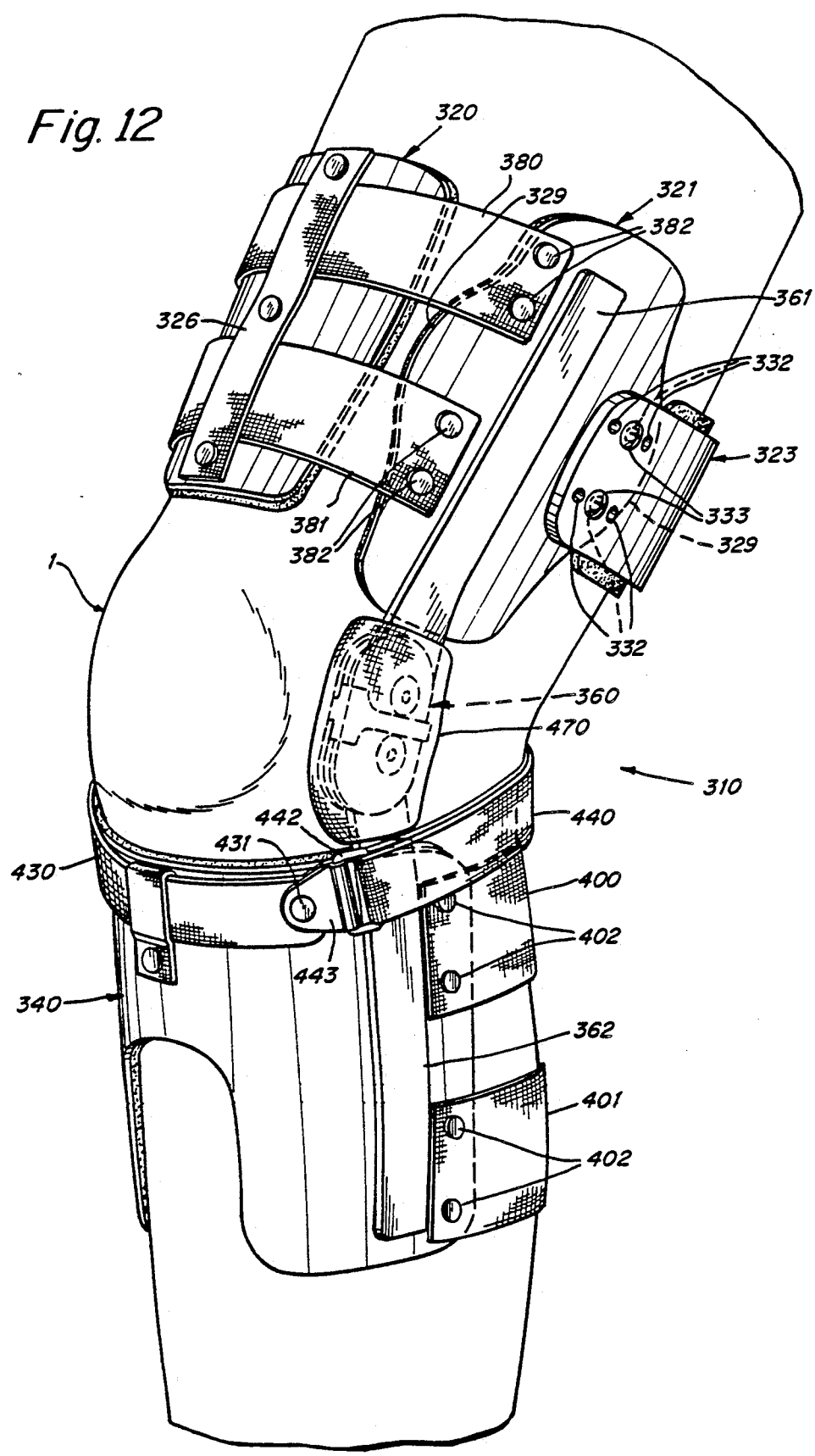
FIG. 12 is a lateral perspective view of a left knee and a third embodiment of the knee brace of this invention.

Non-stretchable upper and lower thigh straps 380 and 381 respectively are each attached by a pair of rivets 382 to an anterior portion of lateral thigh plate 321 and are wrapped in parallel fashion around the front of the thigh (FIGS. 12–14). Upper and lower thigh straps 380, 381 have VELCRO attachment loops on their outer surfaces and a VELCRO attachment hook fastener 383 at their medial (distal) ends. The distal ends of straps 380 and 381 are releasably and adjustably secured by passing through rings 384 attached by tabs 385 and rivets 386 to the medial thigh plate 322 (FIG. 14). The distal ends of straps 380, 381 are then folded back onto themselves such that the VELCRO attachment hooks 383 engage the Velcro loops.

The posterior thigh plate 323 is outwardly curved rectangular plate and extends around a substantial portion of the back of the thigh. At opposite ends of posterior thigh plate 323 there are provided three pairs of apertures 332 disposed in anterior to posterior relation, thereby forming three alternative sets of anterior, central, and posterior apertures. These apertures 322 are positionable over a pair of apertures on each of the lateral and medial side plates 321, 322 respectively and a pair of screws 333 pass through the aligned apertures for connecting the posterior thigh plate with each of the medial and lateral thigh plates. Because posterior thigh plate 323 is outwardly bowed and because of the anterior to posterior arrangement of the three sets of apertures 332, selective engagement of the anterior, central, or posterior sets of apertures 332 provides adjustability as to both depth and width of the thigh engaging members of the knee brace. In addition, a plurality of posterior thigh plates may be provided having different lengths and curvatures to further accomodate differences in the size of the thigh.

Figures 15, 16:
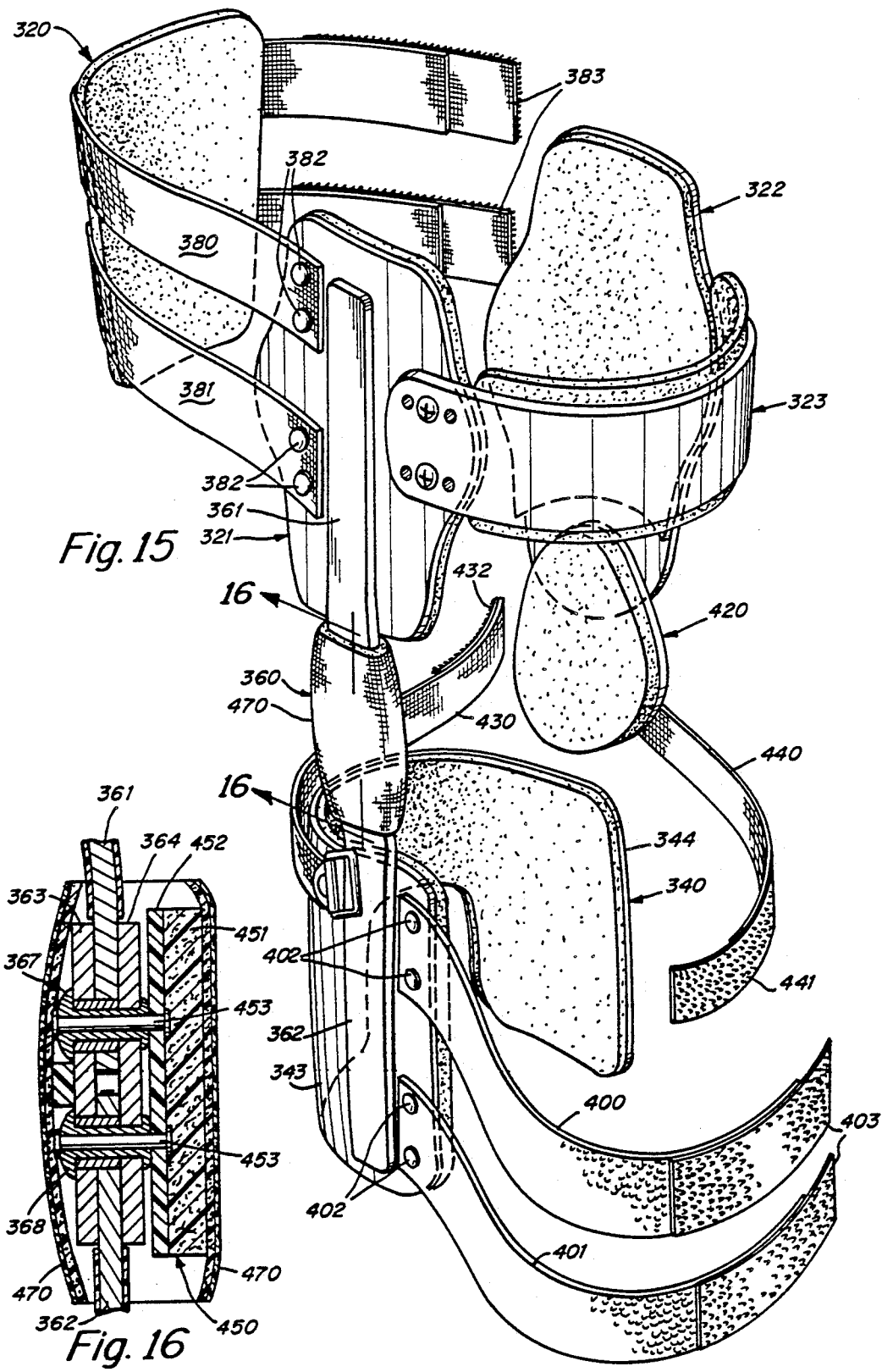
FIG. 15 is an exploded rear perspective view of the knee brace of FIG. 12.
FIG. 16 is a cross-sectional view taken along the section lines 16—16 of FIG 15 showing the dual pivot hinge and lateral condylar pad within the hinge cover.

Knee brace 310 further includes a symmetrical shin cuff 340 having a lateral portion 343, anterior portion 346, and medial portion 344, and a lower anterior cut-out 345 for reduced weight (FIG. 13). Shin cuff 340 has a hard outer shell 341 and soft padding lining 342. A pair of upper and lower calf straps 400 and 401 respectively are attached at one end by a pair of rivets 402 to lateral portion 343 of shin cuff 340 (FIG. 15). Straps 400, 401 have VELCRO attachment loops on their outer surfaces, and at distal end attachments 403 have VELCRO attachment hooks on their outer surfaces. Straps 400, 401 are wrapped in parallel fashion around the back of the leg and are adjustably and releasably connected by passing their distal ends through rings 404 which are attached by tabs 405 and rivets 406 to medial portion 344 of shin cuff 340 (FIG. 14). The distal ends are then folded back such that the VELCRO attachment hooks 403 engage the VELCRO attachments loops.

A polycentric hinge 360 is disposed at the lateral side of the knee. Hinge 360 is substantially identical to hinge 60 of the first embodiment and therefore will not be described in detail. Hinge 360 includes an upper arm 361 attached by three vertically aligned rivets (not shown) to lateral thigh plate 321 and a lower arm 362 which is attached by three vertically aligned rivets (not shown) to lateral portion 343 of shin cuff 340. Hinge 360 has a tubular sleeve 470 covering the central hinge portion.

Polycentric hinge 360 differs from hinge 60 of the first embodiment in that a lateral condylar plate 450 is provided within the interior of sleeve 470 of hinge 360. As shown in FIG. 16, lateral condylar plate 450 includes a hard, rigid backing plate 452 and a soft lining 451 for engaging the lateral side of the knee. Condylar plate 450 is attached by a pair of rivets 453 which pass through upper and lower pivot pins 367 and 368 respectively and by which outer and inner connecting plates 363 and 364 respectively are connected at the joint.

The knee brace 310 of the third embodiment further differs from the first two embodiments in the manner in which the medial plate is connected to the shin cuff. In the third embodiment, the medial plate 420 has a hard outer shell 421 and a softer lining 422 shaped to conform to the medial side of the knee. The medial plate 420 has an upper hinge point 423 at which it is pivotally attached to a lower portion of medial thigh plate 322 by a screw 425 (FIG. 14). The medial plate 420 has a lower connecting point 424 at which it is non-pivotally attached to a pair of front and rear straps 430 and 440 respectively. Non-stretchable front strap 430 is attached at one end to an upper lateral portion of shin cuff 340 by rivet 431 (FIG. 13). Front strap 430 then passes through a loop 436 provided on an upper anterior portion of shin cuff 340, which loop is attached thereto by rivet 437. The distal end of front strap 430 has a VELCRO attachment hook fastener 432 which passes through ring 433 attached by tab 434 and rivet 435 to the lower connecting point 424 on the medial plate 420 (FIG. 14). The distal end is folded back on itself so that the VELCRO attachment hooks 432 engage the VELCRO attachment loops on the exterior of front strap 430. A non-stretchable rear strap is attached at one end by rivet 435 to the lower connecting point 424 of medial plate 420 and wraps around the back of the knee to pass through ring 442 attached by tab 443 and rivet 431 on the upper lateral portion of shin cuff 340. The distal end 441 of rear strap having VELCRO attachment hooks thereon is folded back onto the VELCRO attachment loops on the exterior side of rear strap 440.

In this manner, the front and rear straps 430 and 440 respectively in conjunction with medial plate 420 connect the thigh and shin engaging portions of the knee brace on the medial side of the knee and provide both anterior-posterior and medial-lateral stability. Furthermore, the adjustable straps 430 and 440 provide adjustability for different knee widths.

The components of the third embodiment are preferably made of the same materials described for similar components in the first and second embodiments. If desired, outer bands 90 and 110 as previously described may be wrapped around the brace to further stabilize the same on the leg.

Although certain preferred embodiments of the invention have hereinbefore been described, it will be appreciated that variations of the invention will be perceived by those skilled in the art, which variations are nevertheless within the scope of the invention as defined by the claims appended hereto.

What is claimed is:

1. A modular knee brace comprising:
   a thigh restraining means including lateral and medial thigh plates positionable to engage lateral and medial portions of the thigh respectively, and means for securing the lateral and medial thigh plates to the leg, each of the lateral and medial thigh plates being symmetically shaped to permit interchangeable use on left and right knee braces;
   a shin restraining means;
   a hinge for preventing medial-lateral displacement of the thigh and shin restraining means, the hinge being positionable at the lateral side of the knee and having upper and lower hinge arms and at least one pivot point therebetween;
   means for connecting the upper hinge arm to the lateral thigh plate and the lower hinge arm to the shin restraining means;
   a medial articulation plate to stabilize the brace positionable to engage the medial side of the knee and symmetically shaped to permit interchangeable use on left and right knee braces;
   means for pivotally connecting the medial articulation plate and the medial thigh plate to provide a medial articulation point adjacent the knee from which the plate pivots in a substantially anterior-posterior direction; and
   means for connecting the medial articulation plate and the shin restraining means to restrain anterior movement of the tibia with respect to the femur, the connecting means including an anterior strap extending from the medial articulation plate to the shin restraining means and a posterior strap extending from the medial articulation plate to the shin restraining means.

2. The knee brace of claim 1, wherein the shin restraining means is symmetically shaped to permit interchangeable use on left and right knee braces.

3. The knee brace of claim 1, wherein the thigh restraining means further comprises anterior and posterior thigh plates.

4. The knee brace of claim 3, wherein the posterior thigh plate is arcuate and adjustably connected at opposing ends to the medial and lateral thigh plates.

5. The knee brace of claim 4, wherein the posterior thigh plate has a plurality of apertures at both ends disposed in anterior to posterior relation for adjustable engagement with the lateral and medial thigh plates.

6. A knee brace comprising:
   a thigh restraining means;
   a shin restraining means;
   a hinge for preventing medial-lateral displacement of the thigh and shin restraining means, the hinge being positionable at the lateral side of the knee for connecting the thigh restraining means and the shin restraining means and providing at least one pivot point therebetween;
   a medial plate to stabilize the brace positionable to engage the medial side of the knee and having upper and lower points of attachment for connecting the medial plate to the thigh restraining means and the shin restraining means respectively;
   pivotal connecting means at the upper point of attachment between the medial plate and the thigh restraining means from which the plate pivots in a substantially anterior-posterior direction;
   connecting means for connecting the medial plate to shin restraining means for restraining anterior movement of the tibia with respect to the femur, the connecting means comprising:
      a non-stretchable front strap extending from the medial plate across the front of the leg to a lateral portion of the shin restraining means;
      a non-stretchable rear strap extending from the medial plate around the back of the leg to a lateral portion of the shin restraining means; and
      adjustable connecting means on the front and rear straps for adjusting the lengths of the front and rear straps;
   wherein the knee brace provides both anterior-posterior stability and medial-lateral stability and accommodates knees of different widths.

7. The knee brace of claim 6, wherein the shin restraining means includes a channel means on an anterior portion thereof through which the front strap passes.

8. The knee brace of claim 6, further comprising:
   a lateral plate positionable on the lateral side of the knee and having an inner surface for engaging the lateral side of the knee.

* * * * *

UNITED STATES PATENT AND TRADEMARK OFFICE
CERTIFICATE OF CORRECTION

PATENT NO. : 4,991,571

DATED : February 12, 1991

INVENTOR(S) : Kausek

It is certified that error appears in the above-identified patent and that said Letters Patent is hereby corrected as shown below:

Col. 8, line 48, change "165" to --265--.

Col. 9, line 5, change "70" to --270--.

Col. 10, line 11, change "padding" to --padded--.

Signed and Sealed this

Fourteenth Day of July, 1992

Attest:

DOUGLAS B. COMER

*Attesting Officer*   *Acting Commissioner of Patents and Trademarks*